United States Patent [19]

Bernard et al.

[11] Patent Number: 5,910,438
[45] Date of Patent: Jun. 8, 1999

[54] CLONING AND/OR SEQUENCING VECTOR

[75] Inventors: Philippe Bernard; Philippe Gabant, both of Brussels, Belgium

[73] Assignee: Universite Libre de Bruxelles, Belgium

[21] Appl. No.: 08/379,614

[22] PCT Filed: Aug. 2, 1993

[86] PCT No.: PCT/BE93/00051

§ 371 Date: Jul. 20, 1995

§ 102(e) Date: Jul. 20, 1995

[87] PCT Pub. No.: WO94/03616

PCT Pub. Date: Feb. 17, 1994

[30] Foreign Application Priority Data

Jul. 31, 1992 [BE] Belgium ................................ 9200696

[51] Int. Cl.$^6$ ................................ C12N 1/21; C12N 15/70
[52] U.S. Cl. .................................. 435/252.3; 435/252.33; 435/320.1

[58] Field of Search ................................ 435/320.1, 252.3, 435/252.33; 536/23.1; 530/350

[56] References Cited

PUBLICATIONS

Pierce et al. (1992) Proc. Natl. Acad. Sci. USA 89:2056–2060. Mar. 1992.

*Primary Examiner*—George C. Elliott
*Assistant Examiner*—Robert Schwartzman
*Attorney, Agent, or Firm*—Knobbe Martens Olson & Bear LLP

[57] ABSTRACT

A cloning and/or sequencing vector (1) comprises a nucleotide promoter sequence (3) and a nucleotide sequence (4) coding for a fusion protein active as a poison, which nucleotide sequence (4) is obtained by fusion of a coding nucleotide sequence (5) containing several unique cloning sites with a nucleotide sequence (6) coding for a poison protein, wherein the nucleotide sequences (3) and (4) are incorporated in an autonomous replication vector (2).

14 Claims, 4 Drawing Sheets

SEQ ID NO: 1
SEQUENCE TYPE: Nucleotide and its corresponding protein
SEQUENCE LENGTH: 306 base pairs
MOLECULE TYPE: Plasmid DNA
PROPERTIES: ccdB gene and the CcdB protein of the F plasmid
REFERENCE: Miki et al. 1983a

FIG.2

```
ATG CAG TTT AAG GTT TAC ACC TAT AAA AGA GAG AGC CGT TAT CGT CTG TTT GTG   54
Met Gln Phe Lys Val Tyr Thr Tyr Lys Arg Glu Ser Arg Tyr Arg Leu Phe Val
              5                  10                  15

GAT GTA CAG AGT GAT ATT ATT GAC ACG CCC GGG CGA CGG ATG GTG ATC CCC CTG  108
Asp Val Gln Ser Asp Ile Ile Asp Thr Pro Gly Arg Arg Met Val Ile Pro Leu
         20                  25                  30                  35

GCC AGT GCA CGT CTG CTG TCA GAT AAA GTC TCC CGT GAA CTT TAC CCG GTG GTG  162
Ala Ser Ala Arg Leu Leu Ser Asp Lys Val Ser Arg Glu Leu Tyr Pro Val Val
             40                  45                  50

CAT ATC GGG GAT GAA AGC TGG CGC ATG ATG ACC ACC GAT ATG GCC AGT GTG CCG  216
His Ile Gly Asp Glu Ser Trp Arg Met Met Thr Thr Asp Met Ala Ser Val Pro
 55                  60                  65                  70

GTC TCC GTT ATC GGG GAA GAA GTG GCT GAT CTC AGC CAC CGC GAA AAT GAC ATC  270
Val Ser Val Ile Gly Glu Glu Val Ala Asp Leu Ser His Arg Glu Asn Asp Ile
             75                  80                  85                  90

AAA AAC GCC ATT AAC CTG ATG TTC TGG GGA ATA TAA                          306
Lys Asn Ala Ile Asn Leu Met Phe Trp Gly Ile
                 95
```

Figure 3

SEQ ID NO: 2
SEQUENCE TYPE: Nucleotide and its corresponding protein
SEQUENCE LENGTH: 420 base pairs
MOLECULE TYPE: Plasmid DNA
PROPERTIES: ccdB gene and the CcdB protein of the plasmid pKIL 18

FIG. 3

```
ATG ACC ATG ATT ACG AAT TCG AGC TCG GTA CCC GGG GAT CCT CTA GAG TCG ACC   54
Met Thr Met Ile Thr Asn Ser Ser Ser Val Pro Gly Asn Pro Leu Glu Ser Thr
              5                   10                  15

TGC AGG CAT GCA AGC TTG TCT TTC CAG TTT AAG GTT TAC ACC TAT AAA AGA GAG  108
Cys Arg His Ala Lys Leu Ser Leu Gln Phe Lys Val Tyr Thr Tyr Lys Arg Glu
    20              25                  30                  35

AGC CGT TAT CGT CTG TTT GTG GAT GTA CAG AGT GAT ATT ATT GAC ACG CCG GGG  162
Ser Arg Tyr Arg Leu Phe Val Asp Val Gln Ser Asp Ile Ile Asp Thr Pro Gly
              40                  45                  50

CGA CGG ATG GTG ATC CCC CTG GCC AGT GCA CGT CTG CTG TCA GAT AAA GTC TCC  216
Arg Arg Met Val Ile Pro Leu Ala Ser Ala Arg Leu Leu Ser Asp Lys Val Ser
55                  60                  65                  70

CGT GAA CTT TAC CCG GTG GTG CAT ATC GGG GAT GAA AGC TGG CGC ATG ATG ACC  270
Arg Glu Leu Tyr Pro Val Val His Ile Gly Asp Glu Ser Trp Arg Met Met Thr
         75                  80                  85                  90

ACC GAT ATG GCC AGT GTG CCG GTC TCC GTT ATC GGG GAA GAA GTG GCT GAT CTC  324
Thr Asp Met Ala Ser Val Pro Val Ser Val Ile Gly Glu Glu Val Ala Asp Leu
              95                  100                 105

AGC CAC CGC GAA AAT GAC ATC AAA AAC GCC ATT AAC CTG ATG TTC TGG GGA ATA  378
Ser His Arg Glu Asn Asp Ile Lys Asn Ala Ile Asn Leu Met Phe Trp Gly Ile
             110                 115                 120

TAAATGTCAG GCTCC GTTAT ACACAAGCTA GCTTGGCACT GG                           420
```

FIGURE 4

SEQ ID. NO: 3
SEQUENCE TYPE: Nucleotide and its corresponding protein
SEQUENCE LENGTH: 416 base pairs
MOLECULE TYPE: plasmid DNA
PROPERTIES: ccdB gene and the CcdB protein of the plasmid
pKIL 19

FIG. 4

```
ATG ACC ATG ATT ACG CCA AGC TTG CAT GCC TGC AGG TCG ACT CTA GAG GAT CCC   54
Met Thr Met Ile Thr Pro Ser Leu His Ala Cys Arg Ser Thr Leu Glu Asp Pro
              5                   10                  15

CGG GTA CCG AGC TCG AAT TCA TTG CAG TTT AAG GTT TAC ACC TAT AAA AGA GAG   108
Arg Val Pro Ser Ser Asn Ser Leu Gln Phe Lys Val Tyr Thr Tyr Lys Arg Glu
     20                  25                  30                  35

AGC CGT TAT CGT CTG TTT GTG GAT GTA CAG AGT GAT ATT ATT GAC ACG CCG GGG   162
Ser Arg Tyr Arg Leu Phe Val Asp Val Gln Ser Asp Ile Ile Asp Thr Pro Gly
           40                  45                  50

CGA CGG ATG GTG ATC CCC CTG GCC AGT GCA CGT CTG CTG TCA GAT AAA GTC TCC   216
Arg Arg Met Val Ile Pro Leu Ala Ser Ala Arg Leu Leu Ser Asp Lys Val Ser
55                  60                  65                  70

CGT GAA CTT TAC CCG GTG GTG CAT ATC GGG GAT GAA AGC TGG CGC ATG ATG ACC   270
Arg Glu Leu Tyr Pro Val Val His Ile Gly Asp Glu Ser Trp Arg Met Met Thr
           75                  80                  85                  90

ACC GAT ATG GCC AGT GTG CCG GTC TCC GTT ATC GGG GAA GAA GTG GCT GAT CTC   324
Thr Asp Met Ala Ser Val Pro Val Ser Val Ile Gly Glu Glu Val Ala Asp Leu
                95                  100                 105

AGC CAC CGC GAA AAT GAC ATC AAA AAC GCC ATT AAC CTG ATG TTC TGG GGA ATA   378
Ser His Arg Glu Asn Asp Ile Lys Asn Ala Ile Asn Leu Met Phe Trp Gly Ile
         110                 115                 120

TAAATGTCAG GCTCCGTTAT ACACGAATTA ATTCAGTG                                 416
```

CLONING AND/OR SEQUENCING VECTOR

This application is a 371 of PCT/BE93/00051 filed Aug. 2, 1993.

SUBJECT-MATTER OF THE INVENTION

The invention relates to a cloning and/or sequencing vector which enables recombinant clones to be selected directly.

The invention also relates to the procaryotic cell which is transformed by this vector and to the procaryotic host cell for this vector, as well as to the use of this cloning and sequencing vector for selecting and sequencing recombinant clones.

STATE OF THE ART AND TECHNOLOGICAL BACKGROUND UNDERLYING THE INVENTION

Phage (the M13 series) and plasmid (the pUC series) cloning vectors, containing numerous unique cloning sites, were constructed by Messing et al (P.N.A.S. USA, 79, pp. 3642–3646 (1977), by Norrander et al (Gene, 26, pp. 101–106 (1983) and Yanisch-Perron et al (Gene, 33pp. 103 to 119) (1985)).

The multiple cloning sites (MCS-multiple cloning sites) of these vectors are located in the coding sequence of the LacZ gene.

Discrimination between the transformed cells which harbor a recombinant vector and the cells which harbor a non-recombinant vector is achieved using the "blue screen" technique described by Gronenborn and Messing (Methylation of single-stranded DNA in vitro introduces new restriction endonuclease cleavages sites, Nature, 272, pp. 375–377 (1978)).

However, this "blue screen" technique suffers from the disadvantage of using a screening procedure (discrimination) rather than a procedure for selecting the clones.

Discrimination by screening is based on identifying a clone within a population of clones on the basis of a characteristic (color) which differentiates it. Selection has no need of this characteristic, since it is only recombinant clones which are isolated by this method.

The screening procedure is based on the color of the recombinant clones (white color) and of the non-recombinant clones (blue color). This color is based on inactivation of the marker beta-galactosidase, preventing cleavage of X-gal (5-bromo-4-chloro-3-indolyl β-galactoside). The cell colonies harboring a non-recombinant vector produce a functional beta-galacto-sidase and, by hydrolyzing the X-gal substrate, produce a blue coloration. In general, the insertion of a DNA fragment into the β-galactosidase gene prevents cleavage of the X-gal. For this reason, the cells harboring a recombinant vector have a white color.

Moreover, this complex procedure requires the use of the substrate X-gal which is a product which is very expensive, unstable and awkward to use.

On the other hand, various cloning vectors permitting direct selection (positive selection) of recombinant strains have been described in the scientific literature.

Pierce et al (Proc. Natl. Acad. Sci., vol 89. No. 6, 1992, pp. 2056–2060) describe a vector which comprises the lethal gene sac B from Bacillus amylolique-faciens, integrated into a plasmid derived from the bacteriophage P1 and under the control of a specific *E. coli* promoter.

The promoter of this vector includes a region having several specific cloning sites (cleavage site for a restriction enzyme).

Since the gene sac B encodes levan sucrase, which catalyzes the hydrolysis of sucrose into products which are toxic for *E. coli*, direct selection of the mutants which incorporate a recombinant plasmid is effected on a culture medium containing sucrose. Since the levan sucrase is toxic, even in the absence of sucrose, it is essential, consequently, to repress its synthesis if one wishes to obtain a large number of plasmid copies in the bacterial cytoplasm.

However, it is difficult, if not impossible, to repress the cytotoxic gene completely, particularly if a large number of copies of the vector are required.

Therefore, the impossibility of repressing the cytotoxic gene leads, in phases of producing the plasmid, to the death of the cell and, as a consequence, to selective pressure towards mutated strains (characterized by an inactive lethal gene).

In this case, in order to ensure that the enzyme encoded by the sac B gene does not kill the host cell, it is necessary to incorporate a CI repressor, which regulates the expression of this gene, into the cloning vector.

Furthermore, since sucrose is often incorporated into bacterial culture media, it will be essential to prepare media which are totally free of sucrose in order to carry out these manipulations.

Henrich et al (Gene, vol 42, No. 3, 1986, pp. 345–349) describe a vector which includes the E gene from the bacteriophage φX174, the said E gene being incorporated into the plasmid pUH84 under the control of the Lac promoter.

In this case, the E gene includes six unique restriction sites (located over the whole of the E gene sequence) and encodes gpE, which causes lysis of the *E.coli* cell. In this case, positive selection is effected when a foreign recombinant gene has been inserted into one of the restriction sites.

However, this insertion of a foreign gene into a restriction site located in the sequence of the E gene, encoding gpE, makes it more difficult to sequence the foreign gene and/or amplify it by PCR since, in this case, portions of useless sequences belonging to the E gene encoding gpE are also sequenced, amplified and characterized.

Kuhn et al (Gene, vol 42, No. 3, 1986, pp. 253–263) describe a vector which includes a large gene encoding a restriction enzyme which kills by cleaving the genome of the bacterium, the said gene being incorporated into the plasmid pKG2 under the control of the LacUV5 promoter.

The cloning vectors of the state of the art suffer from the disadvantage of having to be maintained in a host strain which includes the $LacI_q$ repressor in episomal form, or the CI repressor, in order to inactivate the promoter and prevent expression of the killer gene, thus leading to the death of the host strain.

In addition, if it is desired to use this strain to produce a large number of copies of the cloning vectors, the repressor will not be adequate for preventing either a selective pressure which modifies the cytotoxic activity of the vector or a "genetic leakage", that is to say expression of certain copies of the vector and death of the host strain.

Consequently, none of the documents of the state of the art describes a cloning vector which can incorporate large nucleotide fragments, which is easy to manipulate and which can be produced by a microorganism on an industrial scale; that is to say, which can be produced in a large number of copies by a microorganism without bringing about the death of the latter.

OBJECTS OF THE INVENTION

The present invention aims to supply a novel cloning and/or sequencing vector, and also its host strain, which are simple and relatively inexpensive to construct and produce, and which enable recombinant clones to be selected directly, without suffering from the disadvantages of the abovementioned state of the art.

A particular object of the present invention is to obtain a vector which permits specific and certain selection of the recombinant clones.

Another object of the present invention is directed towards obtaining a vector which permits the sequencing, amplification and/or characterization, using the same primer, of any foreign DNA fragment (whatever its size) in the recombinant clones.

An additional object of the present invention is directed towards obtaining a vector which also permits simple extraction of this foreign DNA fragment from the recombinant clone.

A final object of the present invention is directed towards obtaining a host strain for the said vector which allows a large number of copies of the said vector to be produced without bringing about selection pressure which modifies the cytotoxic activity of the said vector or causing the death of the host strain.

CHARACTERISTIC ELEMENTS OF THE INVENTION

The invention relates to a novel cloning and/or sequencing vector which includes, incorporated into an autonomously replicating vector, at least one promoter nucleotide sequence and at least one nucleotide sequence encoding a fusion protein which is active as a poison, the said nucleotide sequence being obtained by fusing a coding nucleotide sequence which includes several unique cloning sites and a nucleotide sequence which encodes a protein poison.

Preferably, the autonomously replicating vector is a recombinant virus or a recombinant plasmid such as a pUC plasmid.

The promoter nucleotide sequence can comprise any promoter, which permits expression of the nucleotide sequence encoding a fusion protein which is active as a poison.

Preferably, this promoter nucleotide sequence consists of the Lac operon promoter.

According to one preferred embodiment of the invention, the unique cloning sites (MCS) of the nucleotide sequence which is fused to the nucleotide sequence which encodes the protein poison are absent from the remainder of the nucleotide sequence of the vector according to the invention.

Advantageously, the nucleotide sequence of the gene which encodes the protein poison comprises all or part of the nucleotide sequence of the wild-type gene which encodes the protein CcdB.

Preferably, the nucleotide sequence of the gene which encodes the protein poison lacks the cleavage site for the restriction enzyme SmaI.

Another aspect of the invention relates to a procaryotic cell which is transformed with the cloning vector according to the invention.

The invention also relates to a procaryotic host cell for the vector according to the invention which possesses a chromosomal $I^q$ and an elevated transformation efficiency, and which possesses a mutation conferring resistance to the poison activity of the fusion protein, and/or which possesses a gene encoding a protein which is an antipoison to the fusion protein.

Preferably, the procaryotic host cell for the vector according to the invention possesses a mutation in the gene encoding subunit A, or in the gene encoding subunit B, of the gyrase, and conferring resistance to the fusion protein, and/or a gene which encodes the protein CcdA which is an antipoison to the fusion protein.

Preferentially, the procaryotic cell is an *Escherichia coli* cell which possesses a mutation which is responsible for replacing arginine 462 with a cysteine in the amino acid sequence of the GyrA polypeptide of the gyrase, thereby conferring resistance to the fusion protein.

Preferably, this procaryotic host cell also possesses the LacI$^q$ mutation.

The present invention also relates to fragments of the vector according to the invention, in particular primers for sequencing and/or amplifying (for example by PCR) the foreign nucleotide fragments inserted into the vector according to the invention.

Preferably, these primers consist of sequences of from 10 to 30 nucleotides which hybridize to nucleotide sequences which are situated on either side of the nucleotide sequence of the vector according to the invention which contains several unique cloning sites.

A final aspect of the invention relates to the use of the vector according to the invention for selecting and sequencing recombinant clones.

DESCRIPTION OF A PREFERRED EMBODIMENT OF THE INVENTION

Figure 1:
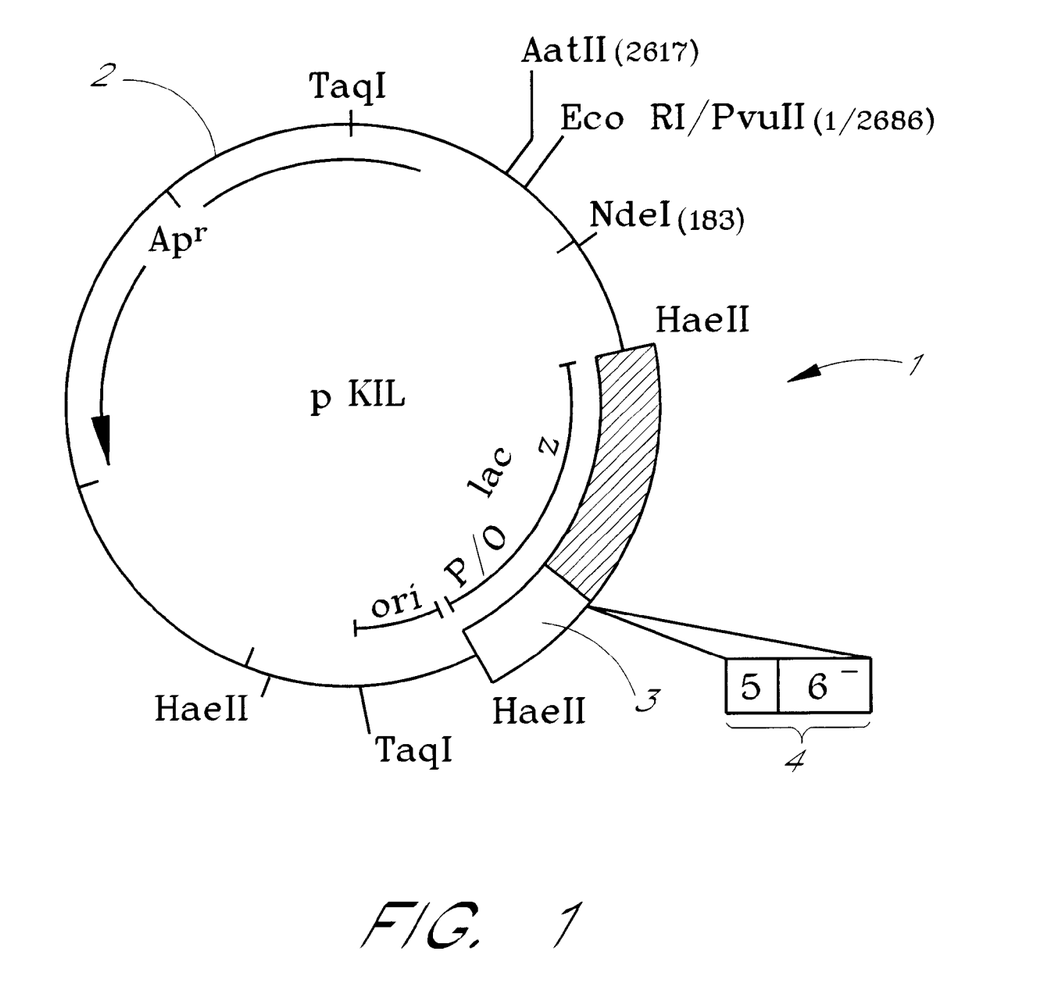
FIG. 1 is a diagrammatic representation of a cloning vector according to the present invention.
Figure 2:
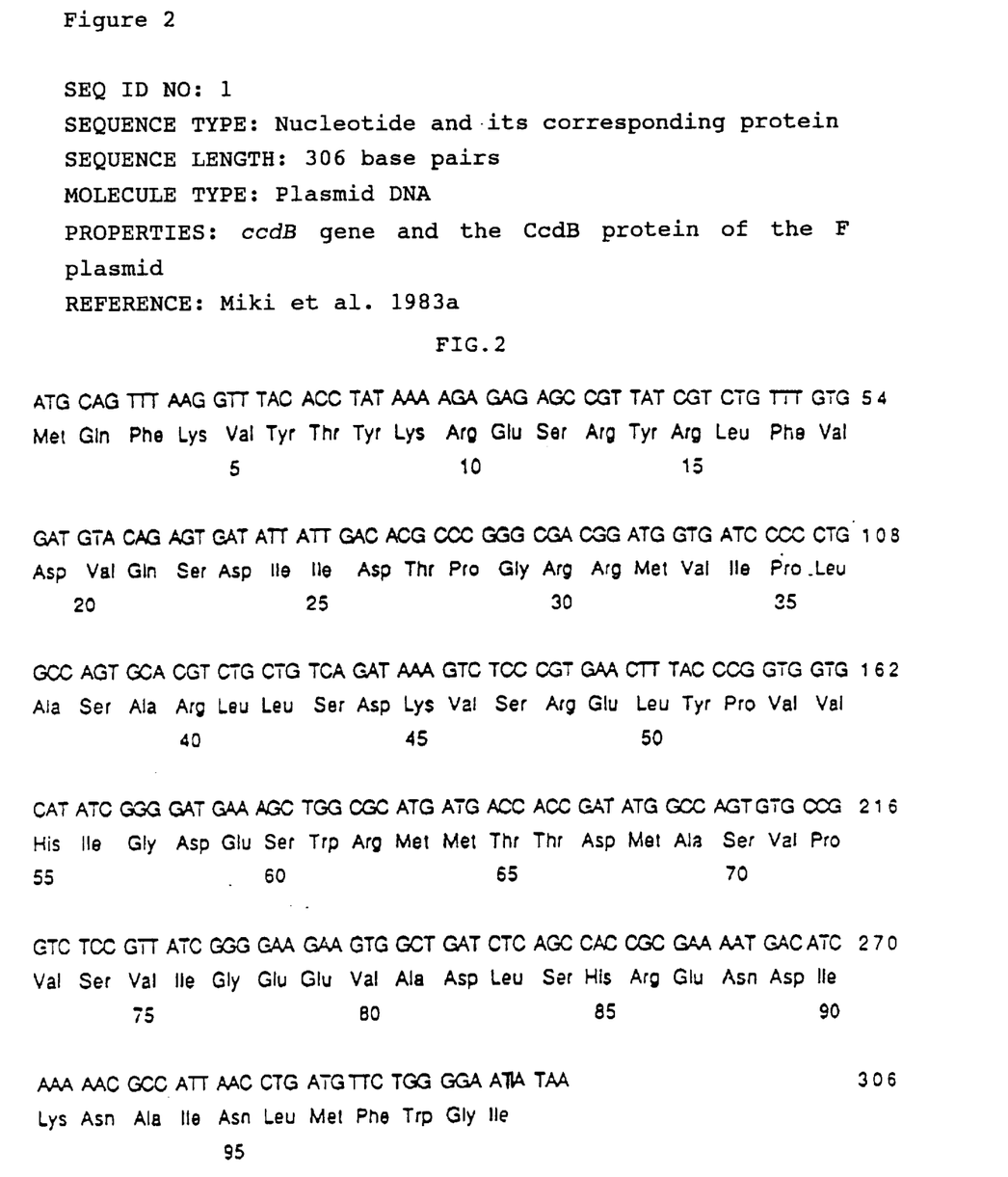
Figure 3:
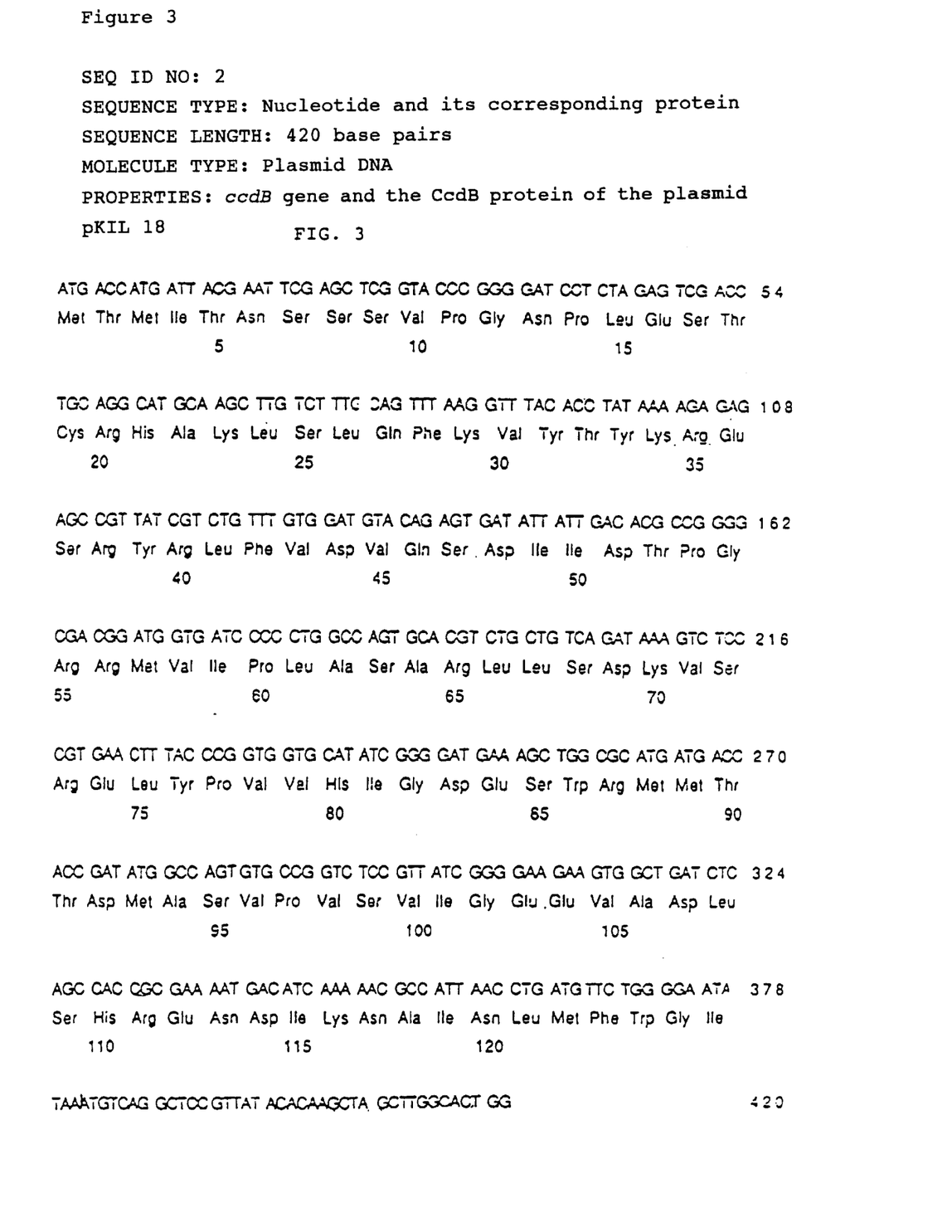
Figure 4:
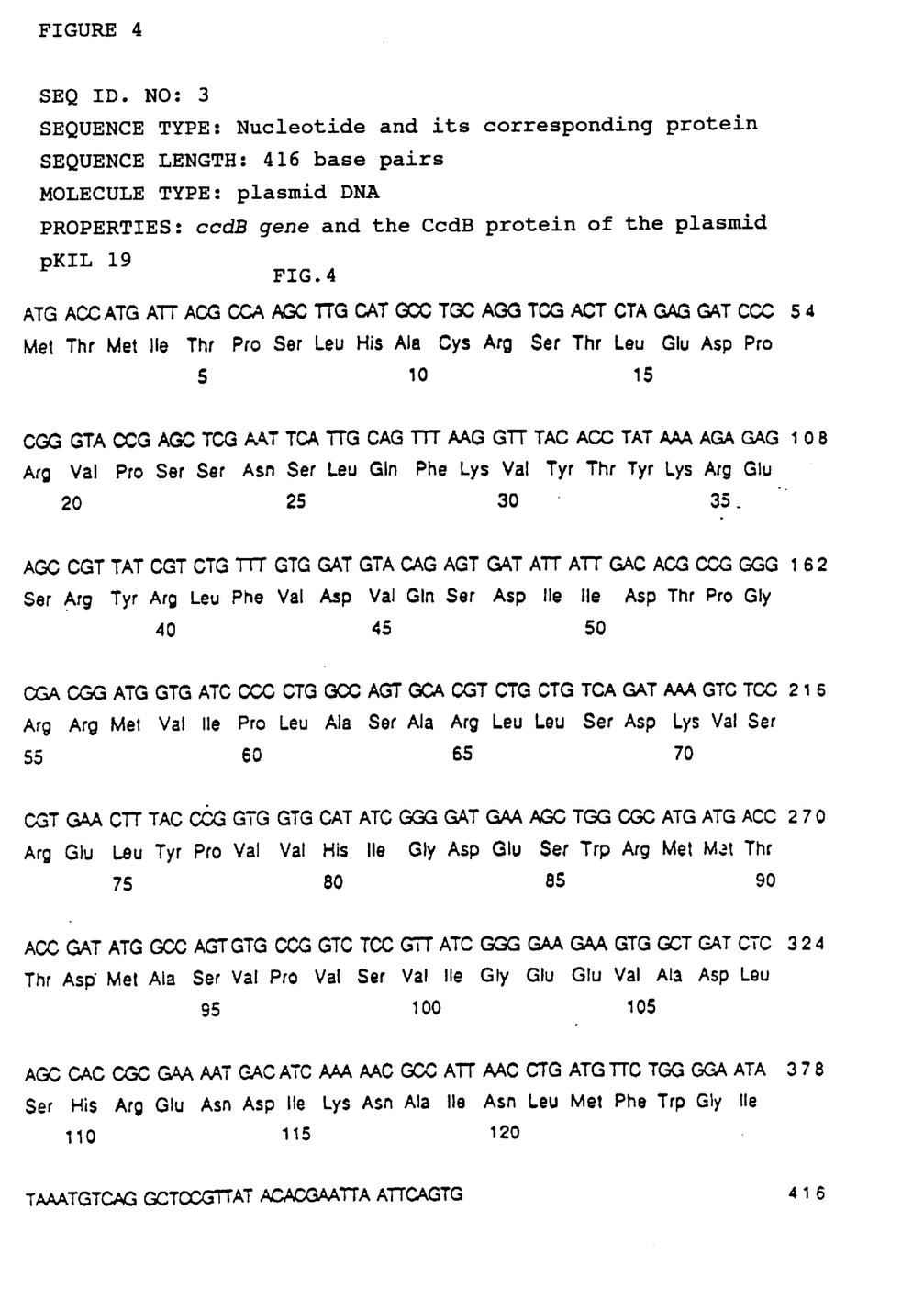

According to the invention, the cloning and/or sequencing vector 1 includes, incorporated into an autonomously replicating vector 2, at least one promoter nucleotide sequence 3 and at least one nucleotide sequence 4 which encodes a fusion protein which is active as a poison, the said nucleotide sequence 4 being obtained by fusing a coding nucleotide sequence 5 (or polylinker) which encompasses several (multiple) unique cloning sites (MCS), and a nucleotide sequence (6) which encodes a protein poison.

An autonomously replicating vector 2 is understood to mean any nucleotide construct, such as a virus or a plasmid (preferably a recombinant plasmid of the PUC series), which is capable of being introduced into a microorganism, of recombining therein and/or of replicating therein.

FIG. 1 shows a diagrammatic representation of a cloning vector according to the present invention, which vector is constructed from a plasmid of the pUC series (pUC18 and pUC19), which is described by Norrander et al (Construction of improved M13 vectors using oligodeoxinucleotide-directed mutagenesis, Gene, 26, pp. 101–106 (1983)) and by Yanisch-Perron et al (Improved M13 phage cloning vectors and host strains: nucleotide sequences of the M13mp18 and pUC19 vectors, Gene, 33, pp. 103–119 (1985)).

A coding nucleotide sequence 5 encompassing several (multiple) unique cloning sites (MCS) is understood to mean a short coding sequence (or polylinker) which comprises several cleavage sites for restriction enzymes.

The advantage of having a polylinker in the vector according to the invention is that different cloning sites are located on a single short sequence, thereby permitting:

rapid sequencing and amplification, using the same primers, of any DNA fragment which is inserted into this vector.

rapid extraction of the cloned fragment, facilitated by the proximity of the restriction sites. Thus, in contrast to the state of the art, this proximity avoids sequencing, amplifying and characterizing useless fragments from other sequences of the vector according to the invention.

Nucleotide sequence 6 encoding a protein poison is understood to mean any (wild-type) nucleotide structure encoding a protein which displays an activity which is naturally poisonous and specific for one or more vital functions of a host cell.

A protein poison is also characterized by the existence of an antidote or antipoison, such as the proteins CcdB and CcdA, the protein Kid and its antagonist Kis, the protein PemK and its antagonist PemI, the protein Doc and its antagonist Phd, the protein HoK and its antagonist Sok, and other poison molecules which are, or are not, of plasmid origin.

In this case, the nucleotide sequence 6 encoding a protein poison consists of the wild-type gene CcdB, which encodes the protein CcdB (control of cell death), obtained from the ccd locus of the F plasmid (SEQ ID NO:1 and SEQ ID NO:4.

The ccd locus of the F plasmid comprises the two wild-type genes ccdA and ccdB, also termed H and G, or letA and letD, which respectively encode proteins of 72 and 101 amino acids (Bex et al, Mini-F encoded proteins; identification of a new 10.5 kilodalton species. EMBO J.2, 1853–1861 (1983); Miki et al, Control of cell division by sex factor F in *Escherichia coli*. I. The 42.84-43.6 F segment couples cell division of the host bacteria with replication of plasmid DNA, J. Mol. Bio., procaryotic cell which is transformed with the cloning 174, 605–625, (1984)).

In *Escherichia coli*, the CcdB protein of the F plasmid is a cytotoxin whose lethal activity is counteracted by the protein CcdA (Karoui et al, Ham22, a mini-F mutation which is lethal to host cell and promotes recA-dependent induction of lambdoid prophage. EMBO J.2, 1863–1868 (1983); Ogura and Hiraga Mini-F plasmid gene that couple host cell division to plasmid proliferation, Proc. Natl. Acad. Sci. USA, 80, 4784–4788 (1983); Miki et al, Control of cell division by sex factor F in *Escherichia coli*. Identification of genes for inhibitor protein and trigger protein on the 42.84-43.6F segment, J. Mol. Biol. 174, 627–646 (1984b)).

The molecular mechanism by which protein CcdB exerts its lethal activity has been elucidated; protein CcdB is poisonous to DNA topoisomerase II.

The type II DNA topoisomerases are essential and ubiquitous enzymes which alter the topology of the DNA by transiently introducing a double-stranded break into the DNA. During the stage of break-religation, topoisomerase II forms an intermediate complex with its DNA substrate in which the enzyme is attached covalently to the 5' end of the cleaved DNA. This transitory intermediate, in which topoisomerase II is linked covalently to the DNA, has been termed the "cleavable complex" (Wang, DNA topoisomerases. Annu. Rev. Biochem. 54, 665–97, 1985; Maxwell & Gellert, Mechanistic aspects of DNA topoisomerases. Advan. Protein Chem. 38, 69–107, 1986; Liu, DNA topoisomerase poisons as antitumor drugs, Annu. Rev. Biochem. 58. 351–375, 1989).

Both in eucaryotes and in procaryotes, the cleavable topoisomerase II-DNA complex is the target of powerful therapeutic agents, including the antibiotics of the "quinolone" family, which act on the gyrase (bacterial topoisomerase II), and anticancer agents (acridines and epipodophyllotoxins), which act on the mammalian topoisomerase II. The therapeutic efficacy of the topoisomerase poisons is correlated with their ability to stabilize the cleavable complex.

DNA topoisomerase II is an essential enzyme in all living entities and is very conserved in the evolution of the species. The CcdB protein thus displays an activity which is potentially cytotoxic for a wide variety of procaryotic species.

The small size of the wild-type ccdB gene allows it to be inserted into plasmids without increasing their size excessively and consequently allows large fragments of foreign DNA to be included therein. Furthermore, given its small size, the wild-type ccdB gene of the F plasmid contains very few restriction sites; it is, therefore, simpler to preserve the uniqueness of the multiple cloning sites (MCS) which are added to it.

Unexpectedly, the inventors observed that the in-phase fusion of the nucleotide sequence 6, encoding protein CcdB, with the coding nucleotide sequence (polylinker 5), comprising several (multiple) unique cloning sites (MCS), gave a nucleotide sequence 4 which encodes a fusion protein which is active as a poison and which makes it possible, as a consequence, to produce vectors for the direct selection of recombinant plasmids (killer selection).

The plasmids which have been obtained allow doubly digested restriction fragments to be cloned in both orientations with respect to the lac promoter. Insertion of a restriction fragment into one of the unique cloning sites interrupts the genetic information of the gene fusion, leading to the synthesis of a gene fusion product which is not functional. Insertional inactivation of the gene fusion ought always to take place when a termination codon is introduced or when a change is made in the reading frame.

The cells which harbor an intact cloning vector of this nature produce a poisonous fusion protein which is functional, and die.

Insertion of a foreign DNA fragment into one of the unique cloning sites of the gene fusion interferes with production of the poison.

The cells which harbor a recombinant vector will be viable while cells which harbor an intact vector will not be viable. This killer selection, by simple culture on a solid medium, makes it possible to eliminate cells which harbor a non-recombinant vector (non-viable clones) and to select recombinant clones (viable clones).

EXAMPLE I

Construction of the plasmid pKIL19

The ccdb gene was amplified by PCR using, as DNA template, the plasmid pULB2208 (Bernard and Couturier, The 41 carboxy-terminal residues of the miniF plasmid CcdA protein are sufficient to antagonize the killer activity of the CcdB protein, Mol. Gen. Genet. 226, 297–304 (1991) as well as synthetic oligonucleotides.

The synthetic oligonucleotide sequences were selected in such a way as to create an EcoRI restriction site on either side of the wild-type ccdB gene in order to be able to reclone this gene in frame with the codons of the MCS19 multiple cloning site and to eliminate the initiation codon of the native ccdb gene. The DNA resulting from the PCR reaction was digested with the enzyme EcoRI and cloned into the EcoRI site of the plasmid pUC19. The resulting plasmid, in which the EcoRI fragment was integrated in the orientation which permitted the ccdB gene, provided with the additional codons corresponding to the MCS19 multiple cloning sites, to be read from the Lac promoter, was termed pKIL2. Plasmid pKIL2 is lethal for a wild-type bacterium (CcdBS sensitive).

pKIL2 also possesses two SmaI sites, one in the multiple cloning sites and the other in the central region of the ccdB gene. The latter was eliminated by site-directed mutagenesis. The resulting plasmid pKIL3, having a unique SmaI site, still has two EcoRI sites. The EcoRI site downstream of the ccdB gene was eliminated by filling in its cohesive ends.

The resulting plasmid, pKIL19 (SEQ ID NO:2 and SEQ ID NO:5), thus possesses a unique EcoRI restriction site within sequence 5, which encompasses the multiple cloning site.

EXAMPLE II
Construction of the plasmid pKIL18

The ccdB gene was amplified by PCR using, as DNA template, plasmid pKIL19 as well as synthetic oligonucleotides. The sequences of the synthetic oligonucleotides were selected in such a way as to create a HindIII site on either side of the ccdb gene in order to be able to reclone this gene in frame with the codons of the MCS18 multiple cloning sites. The DNA resulting from the PCR reaction was digested by the enzyme HindIII and cloned into the HindIII site of the plasmid pUC18. The resulting plasmid, in which the HindIII fragment was integrated in the orientation which permitted the ccdB gene, provided with the additional codons corresponding to the MCS18 multiple cloning sites, to be read from the Lac promoter, was termed pKIL4. Plasmid pKIL4 is lethal for a CcdB$^s$-sensitive bacterium.

The HindIII site downstream of the ccdB gene was eliminated by filling in its cohesive ends. The resultant plasmid, pKIL18 (SEQ ID NO:3 and SEQ ID NO:6) possesses a unique HindIII restriction site as well as a unique SmaI site (since constructed from pKIL19).

EXAMPLE III
Construction of the strains CcdB$^r$ and CcdB$^s$

In order to be able to maintain plasmids pKIL18 and pKIL19 within a bacterium, the latter has to be resistant to the lethal effect of the fusion protein which is active as a poison. Unexpectedly, the chromosomal mutation gyrA462 confers on the strains total resistance to the poisonous effect of the fusion protein.

Moreover, since plasmids pKIL18 and pKIL19 derive directly from plasmids pUC18 and pUC19 and express the ccdB genes from the Lac promoter, it is preferable to maintain these plasmids in a LacI$^q$ strain. Thus, while, in our case, continuous overexpression of these genes does not exert a selection pressure in favor of certain mutations, the LacI$^q$ strain allows expression from the Lac promoter to be reduced and conserves the bacterial machinery, thereby guaranteeing a rapid generation time (increased production of the vector by the strain).

The strain D1210 (Sadler et al Gene 8, pp. 279–300 (1980)), derived from the strain HB101 LacI$^q$, LacY$^+$ (Maniatis et al Molecular Cloning Laboratories Man. Cold Spring Harbor Laboratory New York), and characterized by a chromosomal I$^q$ and increased transformation efficiency, was transformed with the plasmid pCOS2.1. This plasmid, which confers resistance to kanamycin, carries the recA gene from Erwinia chrysanthemi 3665 and allows recombination in E, coli. A lysate of P1 phage was prepared on a CcdB$^R$ gyrA462, zei298::Tn10 strain and used to infect the strain D1210/pCOS2.1. The transductants which were resistant to tetracycline were selected and tested for their resistance or sensitivity to the CcdB protein. One of the CcdB$^R$ transductants was then cured of plasmid pCOS2.1 and termed KIB22.

Strain KIB22 constitutes an ideal host strain for plasmids pKIL18 and pKIL19 while strain D1210 constitutes the ideal host for selecting recombinant plasmids.

Thus, strain KIB22 advantageously possesses an elevated efficiency of DNA extraction (comparable to the yield of the pUC plasmids) and, unexpectedly, resistance to the fusion protein which is encoded by pKIL18 and pKIL19.

Consequently, it is possible to use this microorganism to produce the cloning vector according to the invention on an industrial scale in numerous copies without causing the death of the said microorganism.

The selection is carried out simply by spreading the bacteria on a medium containing IPTG (Isopropyl-Beta-D-thiogalactopyranoside) as well as ampicillin.

Strain KIB22 was deposited with the Laboratorium voor Microbiologie-Bacteriënverzameling (LMG) [Microbiological Laboratory—Bacterial Collection] of the Belgian Coordinated Collections of Microorganisms (BCCM) under No. LMG P-12601.

The cloning vector pKIL19 was deposited with the Laboratorium voor Moleculaire Biologie-Plasmiden Collectie (LMBP) [Molecular Biological Laboratory—Plasmid Collection] of the Belgian Coordinated Collections of Microorganisms (BCCM) under the No. LMBP 2781.

These depositions were made in accordance with the provisions of the Budapest Treaty regarding the International Recognition of the Deposition of Microorganisms.

What is claimed is:

1. An autonomously replicating cloning and/or sequencing vector adapted to transform a procaryotic cell, said vector comprising at least one promoter nucleotide sequence and at least one nucleotide sequence which encodes a fusion protein which is active as a poison to the procaryotic cell, said nucleotide sequence which encodes a fusion protein being obtained by fusing a coding nucleotide sequence, which comprises several cloning sites, and a nucleotide sequence which encodes protein poison CcdB.

2. The vector according to claim 1, wherein said vector is a recombinant plasmid.

3. The vector according to claim 1, wherein the nucleotide sequence which encodes the protein poison lacks the cleavage site for the restriction enzyme SmaI.

4. The vector according to claim 1, wherein the vector corresponds to deposition No. LMBP2781.

5. A procaryotic cell which is transformed with the cloning vector according to claim 1.

6. A method for selecting recombinant clones, comprising:
   inserting an oligodeoxynucleotide into the coding nucleotide sequence of a vector according to claim 1;
   transforming a procaryotic cell susceptible to the poison protein with the vector; and
   selecting recombinant clones which survive.

7. An autonomously replicating cloning and/or sequencing vector adapted to transform a procaryotic cell, said vector being a recombinant virus and comprising at least one promoter nucleotide sequence and at least one nucleotide sequence which encodes a fusion protein which is active as a poison to the procaryotic cell, said nucleotide sequence which encodes a fusion protein being obtained by fusing a coding nucleotide sequence, which comprises several cloning sites, and a nucleotide sequence which encodes protein poison CcdB.

8. An autonomously replicating cloning and/or sequencing vector adapted to transform a procaryotic cell, said vector being a recombinant pUC plasmid and comprising at least one promoter nucleotide sequence and at least one nucleotide sequence which encodes a fusion protein which is active as a poison to the procaryotic cell, said nucleotide sequence which encodes a fusion protein being obtained by fusing a coding nucleotide sequence, which comprises several cloning sites, and a nucleotide sequence which encodes protein poison CccdB.

9. An autonomously replicating cloning and/or sequencing vector adapted to transform a procaryotic cell, said vector comprising at least one repressible promoter nucleotide sequence, which consists of the Lac operon promoter, and at least one nucleotide sequence which encodes a fusion protein which is active as a poison to the procaryotic cell, said nucleotide sequence which encodes a fusion protein being obtained by fusing a coding nucleotide sequence, which comprises several cloning sites, and a nucleotide sequence which encodes protein poison CcdB.

10. An autonomously replicating cloning and/or sequencing vector adapted to transform a procaryotic cell, said vector comprising at least one promoter nucleotide sequence and at least one nucleotide sequence which encodes a fusion protein which is active as a poison to the procaryotic cell, said nucleotide sequence which encodes a fusion protein being obtained by fusing a coding nucleotide sequence, which comprises several cloning sites, and a nucleotide sequence which encodes protein poison CcdB, wherein the cloning sites of the coding nucleotide sequence are absent on the remainder of the nucleotide sequence of the cloning vector.

11. A procaryotic host cell for a cloning vector which encodes a fusion protein which is obtained by fusing a coding nucleotide sequence, which comprises several cloning sites, and a nucleotide sequence which encodes protein poison CcdB, wherein the cell possesses a mutation which confers resistance to the poisonous activity of the fusion protein and/or possesses a gene which encodes a protein which is an antipoison to the fusion protein.

12. The cell according to claim 11, which is an *Escherichia coli* cell, wherein the cell possesses a mutation in which arginine 462 is replaced with a cysteine in the amino acid sequence of the GyrA polypeptide of gyrase.

13. The cell according to claim 11, wherein the cell is that deposited under No. LMGP-12601.

14. The procaryotic host cell of claim 11, wherein the cell possesses a chromosomal $I^q$ and an increased transformation efficiency.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
        (A) LENGTH: 306 base pairs
        (B) TYPE: nucleic acid
        (C) STRANDEDNESS: single
        (D) TOPOLOGY: both     (ii) MOLECULE TYPE: Genomic DNA (iii) HYPOTHETICAL: NO (iv) ANTI-SENSE: NO (v) FRAGMENT TYPE:

(vi) ORIGINAL SOURCE:
    (C) INDIVIDUAL ISOLATE: ccdB gene of plasmid F (ix) FEATURE:
    (A) NAME/KEY: Coding Sequence
    (B) LOCATION: 1...303
    (D) OTHER INFORMATION:

(xi) SEQUENCE DESCRIPTION: SEQ ID NO:1:

```
ATG CAG TTT AAG GTT TAC ACC TAT AAA AGA GAG AGC CGT TAT CGT CTG      48
Met Gln Phe Lys Val Tyr Thr Tyr Lys Arg Glu Ser Arg Tyr Arg Leu
1               5                   10                  15

TTT GTG GAT GTA CAG AGT GAT ATT ATT GAC ACG CCC GGG CGA CGG ATG      96
Phe Val Asp Val Gln Ser Asp Ile Ile Asp Thr Pro Gly Arg Arg Met
                20                  25                  30

GTG ATC CCC CTG GCC AGT GCA CGT CTG CTG TCA GAT AAA GTC TCC CGT     144
Val Ile Pro Leu Ala Ser Ala Arg Leu Leu Ser Asp Lys Val Ser Arg
            35                  40                  45

GAA CTT TAC CCG GTG GTG CAT ATC GGG GAT GAA AGC TGG CGC ATG ATG     192
Glu Leu Tyr Pro Val Val His Ile Gly Asp Glu Ser Trp Arg Met Met
        50                  55                  60

ACC ACC GAT ATG GGC AGT GTG CCG GTC TCC GTT ATC GGG GAA GAA GTG     240
Thr Thr Asp Met Gly Ser Val Pro Val Ser Val Ile Gly Glu Glu Val
65                  70                  75                  80

GCT GAT CTC AGC CAC CGC GAA AAT GAC ATC AAA AAC GCC ATT AAC CTG     288
Ala Asp Leu Ser His Arg Glu Asn Asp Ile Lys Asn Ala Ile Asn Leu
                85                  90                  95

ATG TTC TGG GGA ATA TAA                                             306
Met Phe Trp Gly Ile
                100
```

(2) INFORMATION FOR SEQ ID NO:2:

(i) SEQUENCE CHARACTERISTICS:
        (A) LENGTH: 420 base pairs
        (B) TYPE: nucleic acid
        (C) STRANDEDNESS: single
        (D) TOPOLOGY: both (ii) MOLECULE TYPE: Genomic DNA (iii) HYPOTHETICAL: NO (iv) ANTI-SENSE: NO (v) FRAGMENT TYPE:

(vi) ORIGINAL SOURCE:
    (C) INDIVIDUAL ISOLATE: ccdB gene of pKIL 18

(ix) FEATURE:
    (A) NAME/KEY: Coding Sequence
    (B) LOCATION: 1...378
    (D) OTHER INFORMATION:

(xi) SEQUENCE DESCRIPTION: SEQ ID NO:2:

```
ATG ACC ATG ATT ACG AAT TCG AGC TCG GTA CCC GGG GAT CCT CTA GAG      48
Met Thr Met Ile Thr Asn Ser Ser Ser Val Pro Gly Asp Pro Leu Glu
1               5                   10                  15

TCG ACC TGC AGG CAT GCA AGC TTG TCT TTG CAG TTT AAG GTT TAC ACC      96
Ser Thr Cys Arg His Ala Ser Leu Ser Leu Gln Phe Lys Val Tyr Thr
                20                  25                  30

TAT AAA AGA GAG AGC CGT TAT CGT CTG TTT GTG GAT GTA CAG AGT GAT     144
```

```
Tyr Lys Arg Glu Ser Arg Tyr Arg Leu Phe Val Asp Val Gln Ser Asp
        35              40                  45

ATT ATT GAC ACG CCC GGG CGA CGG ATG GTG ATC CCC CTG GCC AGT GCA    192
Ile Ile Asp Thr Pro Gly Arg Arg Met Val Ile Pro Leu Ala Ser Ala
    50                  55                  60

CGT CTG CTG TCA GAT AAA GTC TCC CGT GAA CTT TAC CCG GTG GTG CAT    240
Arg Leu Leu Ser Asp Lys Val Ser Arg Glu Leu Tyr Pro Val Val His
65              70                  75                  80

ATC GGG GAT GAA AGC TGG CGC ATG ATG ACC ACC GAT ATG GCC AGT GTG    288
Ile Gly Asp Glu Ser Trp Arg Met Met Thr Thr Asp Met Ala Ser Val
                85                  90                  95

CCG GTC TCC GTT ATC GGG GAA GAA GTG GCT GAT CTC AGC CAC CGC GAA    336
Pro Val Ser Val Ile Gly Glu Glu Val Ala Asp Leu Ser His Arg Glu
            100                 105                 110

AAT GAC ATC AAA AAC GCC ATT AAC CTG ATG TTC TGG GGA ATA TAAATGTCAG 388
Asn Asp Ile Lys Asn Ala Ile Asn Leu Met Phe Trp Gly Ile
            115                 120                 125

GCTCCGTTAT ACACAAGCTA GCTTGGCACT GG                                420

(2) INFORMATION FOR SEQ ID NO:3:

(i) SEQUENCE CHARACTERISTICS:
        (A) LENGTH: 416 base pairs
        (B) TYPE: nucleic acid
        (C) STRANDEDNESS: single
        (D) TOPOLOGY: both (ii) MOLECULE TYPE: Genomic DNA (iii) HYPOTHETICAL: NO (iv) ANTI-SENSE: NO (v) FRAGMENT TYPE:

(vi) ORIGINAL SOURCE:
        (C) INDIVIDUAL ISOLATE: ccdB gene of plasmid pKIL 19

(ix) FEATURE:
        (A) NAME/KEY: Coding Sequence
        (B) LOCATION: 1...378
        (D) OTHER INFORMATION:

(xi) SEQUENCE DESCRIPTION: SEQ ID NO:3:

ATG ACC ATG ATT ACG CCA AGC TTG CAT GCC TGC AGG TCG ACT CTA GAG    48
Met Thr Met Ile Thr Pro Ser Leu His Ala Cys Arg Ser Thr Leu Glu
1               5                   10                  15

GAT CCC CGG GTA CCG AGC TCG AAT TCA TTG CAG TTT AAG GTT TAC ACC    96
Asp Pro Arg Val Pro Ser Ser Asn Ser Leu Gln Phe Lys Val Tyr Thr
                20                  25                  30

TAT AAA AGA GAG AGC CGT TAT CGT CTG TTT GTG GAT GTA CAG AGT GAT    144
Tyr Lys Arg Glu Ser Arg Tyr Arg Leu Phe Val Asp Val Gln Ser Asp
        35                  40                  45

ATT ATT GAC ACG CCG GGG CGA CGG ATG GTG ATC CCC CTG GCC AGT GCA    192
Ile Ile Asp Thr Pro Gly Arg Arg Met Val Ile Pro Leu Ala Ser Ala
    50                  55                  60

CGT CTG CTG TCA GAT AAA GTC TCC CGT GAA CTT TAC CCG GTG GTG CAT    240
Arg Leu Leu Ser Asp Lys Val Ser Arg Glu Leu Tyr Pro Val Val His
65              70                  75                  80

ATC GGG GAT GAA AGC TGG CGC ATG ATG ACC ACC GAT ATG GCC AGT GTG    288
Ile Gly Asp Glu Ser Trp Arg Met Met Thr Thr Asp Met Ala Ser Val
                85                  90                  95

CCG GTC TCC GTT ATC GGG GAA GAA GTG GCT GAT CTC AGC CAC CGC GAA    336
Pro Val Ser Val Ile Gly Glu Glu Val Ala Asp Leu Ser His Arg Glu
            100                 105                 110
```

```
AAT GAC ATC AAA AAC GCC ATT AAC CTG ATG TTC TGG GGA ATA TAAATGTCAG   388
Asn Asp Ile Lys Asn Ala Ile Asn Leu Met Phe Trp Gly Ile
            115                 120                 125

GCTCCGTTAT ACACGAATTA ATTCAGTG                                        416
```

(2) INFORMATION FOR SEQ ID NO:4:

(i) SEQUENCE CHARACTERISTICS:
        (A) LENGTH: 101 amino acids
        (B) TYPE: amino acids
        (C) STRANDEDNESS: single
        (D) TOPOLOGY: linear     (ii) MOLECULE TYPE: protein     (iii) HYPOTHETICAL: NO     (iv) ANTI-SENSE: NO     (v) FRAGMENT TYPE: internal     (vi) ORIGINAL SOURCE:

(xi) SEQUENCE DESCRIPTION: SEQ ID NO:4:

```
Met Gln Phe Lys Val Tyr Thr Tyr Lys Arg Glu Ser Arg Tyr Arg Leu
 1               5                  10                  15

Phe Val Asp Val Gln Ser Asp Ile Ile Asp Thr Pro Gly Arg Arg Met
            20                  25                  30

Val Ile Pro Leu Ala Ser Ala Arg Leu Leu Ser Asp Lys Val Ser Arg
        35                  40                  45

Glu Leu Tyr Pro Val Val His Ile Gly Asp Glu Ser Trp Arg Met Met
         50                  55                  60

Thr Thr Asp Met Gly Ser Val Pro Val Ser Val Ile Gly Glu Glu Val
65                  70                  75                  80

Ala Asp Leu Ser His Arg Glu Asn Asp Ile Lys Asn Ala Ile Asn Leu
                85                  90                  95

Met Phe Trp Gly Ile
            100
```

(2) INFORMATION FOR SEQ ID NO:5:

(i) SEQUENCE CHARACTERISTICS:
        (A) LENGTH: 126 amino acids
        (B) TYPE: amino acids
        (C) STRANDEDNESS: single
        (D) TOPOLOGY: linear     (ii) MOLECULE TYPE: protein     (iii) HYPOTHETICAL: NO     (iv) ANTI-SENSE: NO     (v) FRAGMENT TYPE: internal     (vi) ORIGINAL SOURCE:

(xi) SEQUENCE DESCRIPTION: SEQ ID NO:5:

```
Met Thr Met Ile Thr Asn Ser Ser Val Pro Gly Asp Pro Leu Glu
 1               5                  10                  15

Ser Thr Cys Arg His Ala Ser Leu Ser Leu Gln Phe Lys Val Tyr Thr
            20                  25                  30

Tyr Lys Arg Glu Ser Arg Tyr Arg Leu Phe Val Asp Val Gln Ser Asp
        35                  40                  45

Ile Ile Asp Thr Pro Gly Arg Arg Met Val Ile Pro Leu Ala Ser Ala
    50                  55                  60
```

```
Arg Leu Leu Ser Asp Lys Val Ser Arg Glu Leu Tyr Pro Val Val His
65              70                  75                  80

Ile Gly Asp Glu Ser Trp Arg Met Met Thr Thr Asp Met Ala Ser Val
                85                  90                  95

Pro Val Ser Val Ile Gly Glu Glu Val Ala Asp Leu Ser His Arg Glu
                100                 105                 110

Asn Asp Ile Lys Asn Ala Ile Asn Leu Met Phe Trp Gly Ile
                115                 120             125

(2) INFORMATION FOR SEQ ID NO:6:

(i) SEQUENCE CHARACTERISTICS:
        (A) LENGTH: 126 amino acids
        (B) TYPE: amino acids
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:6:

Met Thr Met Ile Thr Pro Ser Leu His Ala Cys Arg Ser Thr Leu Glu
1               5                   10                  15

Asp Pro Arg Val Pro Ser Ser Asn Ser Leu Gln Phe Lys Val Tyr Thr
                20                  25                  30

Tyr Lys Arg Glu Ser Arg Tyr Arg Leu Phe Val Asp Val Gln Ser Asp
                35                  40                  45

Ile Ile Asp Thr Pro Gly Arg Arg Met Val Ile Pro Leu Ala Ser Ala
                50                  55                  60

Arg Leu Leu Ser Asp Lys Val Ser Arg Glu Leu Tyr Pro Val Val His
65              70                  75                  80

Ile Gly Asp Glu Ser Trp Arg Met Met Thr Thr Asp Met Ala Ser Val
                85                  90                  95

Pro Val Ser Val Ile Gly Glu Glu Val Ala Asp Leu Ser His Arg Glu
                100                 105                 110

Asn Asp Ile Lys Asn Ala Ile Asn Leu Met Phe Trp Gly Ile
                115                 120             125
```